(12) United States Patent
Govari et al.

(10) Patent No.: US 7,060,075 B2
(45) Date of Patent: Jun. 13, 2006

(54) DISTAL TARGETING OF LOCKING SCREWS IN INTRAMEDULLARY NAILS

(75) Inventors: Assaf Govari, Haifa (IL); Avinoam Dayan, Zichron Yacob (IL); Dale G. Davison, Warsaw, IN (US); Thomas G. Ferro, Fort Wayne, IN (US)

(73) Assignee: Biosense, Inc.

( * ) Notice: Subject to any disclaimer, the term of this patent is extended or adjusted under 35 U.S.C. 154(b) by 714 days.

(21) Appl. No.: 10/198,514

(22) Filed: Jul. 18, 2002

(65) Prior Publication Data
US 2004/0034355 A1 Feb. 19, 2004

(51) Int. Cl.
*A61B 17/17* (2006.01)

(52) U.S. Cl. ............................................. 606/98
(58) Field of Classification Search ................. 606/96, 606/97, 98, 102
See application file for complete search history.

(56) References Cited

U.S. PATENT DOCUMENTS

| | | | |
|---|---|---|---|
| 3,672,352 A | 6/1972 | Summers | |
| 4,114,151 A | 9/1978 | Denne et al. | |
| 4,198,987 A | 4/1980 | Cain et al. | |
| RE30,366 E | 8/1980 | Rasor et al. | |
| 4,262,632 A | 4/1981 | Hanton et al. | |
| 4,361,153 A | 11/1982 | Slocum et al. | |
| 4,407,296 A | 10/1983 | Anderson | |
| 4,485,813 A | 12/1984 | Anderson et al. | |
| 4,532,932 A | 8/1985 | Batty, Jr. | |
| 4,610,256 A | 9/1986 | Wallace | |
| 4,621,628 A | 11/1986 | Brudermann | |
| 4,650,547 A | 3/1987 | Gough | |
| 4,796,643 A | 1/1989 | Nakazawa et al. | |
| 4,815,469 A | 3/1989 | Cohen et al. | |
| 4,846,191 A | 7/1989 | Brockway et al. | |
| 4,967,755 A | 11/1990 | Pohndorf | |
| 5,028,918 A | 7/1991 | Giles et al. | |
| 5,067,491 A | 11/1991 | Taylor, II et al. | |
| 5,105,190 A | 4/1992 | Kip et al. | |
| 5,105,829 A | 4/1992 | Fabian et al. | |
| 5,127,913 A | 7/1992 | Thomas, Jr. | |

(Continued)

FOREIGN PATENT DOCUMENTS

DE   30 11 671 A1   10/1981

(Continued)

OTHER PUBLICATIONS

Dargie, Henry J. "Diagnosis and Management of Heart Failure", BMJ 1994;308:321-8.

(Continued)

*Primary Examiner*—David O. Reip
(74) *Attorney, Agent, or Firm*—Louis J. Capezzuto (57) ABSTRACT

In a distal targeting system a hand-held location pad is integral with a guide section for a drill or similar surgical instrument, and has a plurality of magnetic field generators. A sensor, such as a wireless sensor, having a plurality of field transponders, is disposed in an orthopedic appliance, such as an intramedullary nail. The sensor is capable of detecting and discriminating the strength and direction of the different fields generated by the field generators. Control circuitry, preferably located in the location pad is responsive to a signal of the sensor, and determines the displacement and relative directions of an axis of the guide section, and a bore in the orthopedic appliance. A screen display and optional speaker in the location pad provide an operator-perceptible indication that enables the operator to adjust the position of the guide section so as to align its position and direction with the bore.

69 Claims, 8 Drawing Sheets

U.S. PATENT DOCUMENTS

| | | | |
|---|---|---|---|
| 5,252,962 A | 10/1993 | Urbas et al. |
| 5,279,309 A | 1/1994 | Taylor |
| 5,300,120 A | 4/1994 | Knapp et al. |
| 5,322,063 A | 6/1994 | Allen et al. |
| 5,325,873 A | 7/1994 | Hirschi et al. |
| 5,330,520 A | 7/1994 | Maddison et al. |
| 5,353,800 A | 10/1994 | Pohndorf et al. |
| 5,398,691 A | 3/1995 | Martin et al. |
| 5,404,877 A | 4/1995 | Nolan et al. |
| 5,411,503 A | 5/1995 | Hollstien |
| 5,417,688 A | 5/1995 | Elstrom et al. |
| 5,422,636 A | 6/1995 | Urbas et al. |
| 5,435,310 A | 7/1995 | Sheehan et al. |
| 5,481,262 A | 1/1996 | Urbas et al. |
| 5,513,636 A | 5/1996 | Palti |
| 5,540,691 A | 7/1996 | Elstrom et al. |
| 5,551,427 A | 9/1996 | Altman |
| 5,564,434 A | 10/1996 | Halperin et al. |
| 5,566,676 A | 10/1996 | Rosenfeldt et al. |
| 5,584,838 A | 12/1996 | Rona |
| 5,674,288 A | 10/1997 | Knapp et al. |
| 5,702,421 A | 12/1997 | Schneidt |
| 5,704,352 A | 1/1998 | Tremblay et al. |
| 5,715,827 A | 2/1998 | Corl et al. |
| 5,716,407 A | 2/1998 | Knapp et al. |
| 5,725,552 A | 3/1998 | Kotula et al. |
| 5,725,578 A | 3/1998 | Knapp et al. |
| 5,743,267 A | 4/1998 | Nikolic et al. |
| 5,833,603 A | 11/1998 | Kovacs et al. |
| 5,855,609 A | 1/1999 | Knapp |
| 5,913,820 A | 6/1999 | Bladen |
| 5,957,966 A | 9/1999 | Schroeppel et al. |
| 5,963,132 A | 10/1999 | Yoakum |
| 5,977,431 A | 11/1999 | Knapp et al. |
| 5,993,395 A | 11/1999 | Shulze |
| 5,999,857 A | 12/1999 | Weijand et al. |
| 6,021,352 A | 2/2000 | Christopherson et al. |
| 6,034,296 A | 3/2000 | Elvin et al. |
| 6,053,873 A | 4/2000 | Govari et al. |
| 6,053,918 A | 4/2000 | Spievack |
| 6,074,394 A | 6/2000 | Krause |
| 6,106,476 A | 8/2000 | Corl et al. |
| 6,113,553 A | 9/2000 | Chubbuck |
| 6,115,636 A | 9/2000 | Ryan |
| 6,117,086 A | 9/2000 | Shulze |
| 6,140,740 A | 10/2000 | Porat et al. |
| 6,159,156 A | 12/2000 | Van Bockel |
| 6,162,228 A | 12/2000 | Durham |
| 6,174,322 B1 | 1/2001 | Schneidt |
| 6,181,973 B1 | 1/2001 | Ceron et al. |
| 6,185,464 B1 | 2/2001 | Bonner et al. |
| 6,214,029 B1 | 4/2001 | Thill et al. |
| 6,216,029 B1 | 4/2001 | Paltieli |
| 6,234,973 B1 | 5/2001 | Meador et al. |
| 6,237,398 B1 | 5/2001 | Porat et al. |
| 6,239,724 B1 | 5/2001 | Doron et al. |
| 6,240,322 B1 | 5/2001 | Peterfoso et al. |
| 6,259,937 B1 | 7/2001 | Schulman et al. |
| 6,261,247 B1 | 7/2001 | Ishikawa et al. |
| 6,277,078 B1 | 8/2001 | Porat et al. |
| 6,309,350 B1 | 10/2001 | Van Tassel et al. |
| 6,312,465 B1 | 11/2001 | Griffin et al. |
| 6,328,699 B1 | 12/2001 | Eigler et al. |
| 6,328,727 B1 | 12/2001 | Frazier et al. |
| 6,370,418 B1 | 4/2002 | Bernoski |
| 6,374,134 B1 | 4/2002 | Bladen et al. |
| 6,385,482 B1 | 5/2002 | Boksberger et al. |
| 6,405,091 B1 | 6/2002 | Vachon et al. |
| 6,409,674 B1 | 6/2002 | Brockway et al. |
| 6,411,842 B1 | 6/2002 | Cigaina et al. |
| 6,442,413 B1 | 8/2002 | Silver |
| 2002/0052604 A1 | 5/2002 | Simon et al. |

FOREIGN PATENT DOCUMENTS

| | | |
|---|---|---|
| DE | 3219558 A1 | 12/1983 |
| DE | 299 09 923 U1 | 10/1999 |
| EP | 0 021 451 A1 | 7/1981 |
| EP | 0 053 976 A2 | 6/1982 |
| EP | 420177 A1 | 4/1991 |
| EP | 0 646 365 A1 | 4/1995 |
| EP | 0 897 690 A1 | 2/1999 |
| EP | 1 004 267 A2 | 5/2000 |
| JP | 60-70324 A | 4/1985 |
| WO | WO 83/03348 A1 | 10/1983 |
| WO | WO 83/02626 A1 | 2/1993 |
| WO | WO 94/04938 A1 | 3/1994 |
| WO | WO 96/05768 A1 | 2/1996 |
| WO | WO 97/13467 A1 | 4/1997 |
| WO | WO 97/33513 A1 | 9/1997 |
| WO | WO 99/17095 A1 | 4/1999 |
| WO | WO 99/34453 AL | 7/1999 |
| WO | WO 99/34731 A1 | 7/1999 |
| WO | WO 99/48419 A1 | 9/1999 |
| WO | WO 00/16686 A2 | 3/2000 |
| WO | WO 00/16686 A3 | 3/2000 |
| WO | WO 00/32092 A1 | 6/2000 |
| WO | WO 00 74557 A1 | 12/2000 |
| WO | WO 01/36014 A2 | 5/2001 |
| WO | WO 02/38082 A1 | 5/2002 |

OTHER PUBLICATIONS

Stevenson, LW & Perloff, JK "The Limited Reliability of Physical Signs for Estimating Hemodynamics in Chronic Heart Failure", JAMA 1989;261, No. 6:884-888.

Chakko S et al. "Clinical, Radiographic, and Hemodynamic Correlations in Chronic Congestive Heart Failure: Conflicting Results May Lead to Inappropriate Care", AJM 1991;90:353-359.

Stevenson LW "Tailored Therapy Before Transplantation for Treatment of Advanced Heart Failure: Effective Use of Vasodilators and Diuretics", J Heart Lung Transplant 1991;10:468-76.

Stevenson LW et al. "Poor Survival of Patients with Idopathic Cardiomyopathy Considered Too Well for Transplantation", AJM 1987;83:871-876.

Steinhaus David M et al. "Initial Experience with an Implantable Hemodynamic Monitor", Circulation 1996;93No. 4:745-752.

Ohlsson A et al. "Continuous Ambulatory Haemodynamic Monitoring with an Implantable System", European Heart Journal 1998;19:174-184.

DISTAL TARGETING OF LOCKING SCREWS IN INTRAMEDULLARY NAILS

BACKGROUND OF THE INVENTION

1. Field of the Invention

This invention relates to intramedullary nails for use in fracture management. More particularly, this invention relates to placement of locking members in intramedullary nails by improved intraoperative distal targeting.

2. Description of the Related Art

Since the development of intramedullary nails for use in orthopedic surgery to manage bone fractures, it has been common practice to fix the bone with respect to the nail by placing locking members through holes drilled through cortical bone in alignment with holes that are pre-drilled transversely in the nail. The procedure has presented technical difficulties, as the pre-drilled holes in the nail are not generally visible to the surgeon, and are difficult to localize and to align with surgical drills and placement instruments, so as to receive the locking members.

Placement of the holes in the cortical bone under X-ray or fluoroscopic guidance has been undertaken in the past, often in combination with complex mechanical alignment devices such C-arms, and stereotactic frames. This approach has proven to be unsatisfactory, due to difficulties in obtaining precise alignment, and maintaining alignment without unduly increasing radiation exposure of the operator, other operating room personnel, and the patient. Attempts to limit radiation exposure by offsetting the drill from the X-ray beam have also not been entirely successful. The use of such procedures has often extended operating time and has increased operative risk and mortality.

Sensors have long been employed to aid in positioning surgical instruments and manipulators. For example, in U.S. Pat. No. 5,279,309, it is proposed to place light emitting beacons on a patient's body in order to establish a frame of reference to locate the relative position of a sensor relative to the beacons in three dimensions. This disclosure is advantageous in situations where direct vision is possible, for example, for robotic manipulators.

More recently magnetic field sensors have been employed in conjunction with intramedullary nails in order to improve localization of the locking holes, and alignment of the locking members.

The patent document WO 93/02626 proposes the use of two or more magnetic driver coils inside a probe that is insertable into a hollow splint such as a nail. A yoke having detection coils on opposite sides of the splint detects the magnetic fields. A maximum signal indicates alignment with a hole in the splint.

The patent document WO 97/13467 discloses the fixation of two electromagnetic drivers in a rod, which is then introduced along an intramedullary nail. In a variation of this arrangement, a neodymium magnet is positioned on the rod, or as plugs to the nail hole. A detector having four coils is used to determine the direction the probe needs to move in order to be centered on the nail hole. Use of a second detector, disposed at a 45-degree angle to the first, permits 3-dimensional localization of the probe.

U.S. Pat. No. 5,411,503 discloses the use of a probe, which is insertable into an intramedullary nail after a fracture has been reduced and the nail has been implanted. A hand-held guide moved about by the surgeon is used to achieve and maintain the proper alignment of a drill or other instrument used in the placement of transverse locking screws. A display unit, connected by electronic cables to the probe and guide, presents visual images that graphically indicate the manner in which the guide must be moved to bring it into proper alignment. Two orthogonal electromagnetic drive coils are embedded near one end of the nail, each having a magnetic axis in parallel alignment with, and at a fixed distance from the axis of a transverse hole. The coils are intermittently driven in non-overlapping time intervals. Multiple receiving coils or Hall effect transducers are placed in the guide, and alignment of the guide is indicated by null signals.

U.S. Pat. No. 5,127,913 proposes to dispose neodymium magnets in a probe that is inserted in the hollow interior of an intramedullary nail. The probe carries a plurality of high-energy magnets having magnetic poles oriented along an axis transverse to a longitudinal axis of the probe, and concentric with an axis of the distal locking holes of the intramedullary nail. An indicator aligns the insert member and the magnets at an aligned position so that the axes of the magnets and distal locking holes are aligned. A single detector magnet for detecting a magnetic field generated by the aligned high-energy magnets through the distal locking holes is disposed exterior to the bone, enabling the operator to mark the location of the locking holes. This arrangement does not provide an indication of a desired direction to move a surgical tool, and is relatively insensitive to deviations when the tool is near an optimum location.

In U.S. Pat. No. 5,584,838 an arrangement is proposed for generating a magnetic field within an intramedullary nail, which has a maximum strength along an axis of a transverse locking hole, and which decreases in strength in directions radially away from the axis. A drill guide has two mounted sensor arrangements at axially spaced locations, each of which has a plurality of sensors at angularly spaced locations, and spaced radially from an opening through the drill guide. This arrangement is responsive to a deviation of the drill opening in the drill guide from coaxial alignment with the axis of the locking hole, and provides a perceptible indication of a radial direction from the drill opening to the axis.

U.S. Pat. No. 6,074,394 proposes using a targeting device having at least two magnetic field communication units to achieve distal targeting. The device consists of a receiver and a transmitter producing multi-axis pulsed direct current magnetic signals in each of three orthogonal planes. One of the communication units is carried in a fixed position by a drill guide and a second of the communication units is in a fixed, offset position relative to an implant connector. The position and orientation of the drill guide relative to the implant connector are determined by the transmission of the pulsed direct current magnetic signal from the transmitting unit and receiving that signal at the receiver. The signals provide the position and location of the communication units in relation to one another. Alignment of the drill guide with the connector is aided by viewing a virtual representation of the position and orientation of the connector and drill guide on a console having a fixed location. This arrangement is somewhat inconvenient for the operator, as it is continually necessary to reference the display, or to obtain callouts from an assistant viewing the fixed console.

SUMMARY OF THE INVENTION

It is therefore a primary object of some aspects of the present invention to provide a compact handheld unit including magnetic field generators to localize bores in an orthopedic appliance such as an intramedullary nail.

It is another object of some aspects of the present invention to provide a distal targeting system having a handheld location pad which is insensitive to magnetically-responsive material in its area of operation.

It is a further object of some aspects of the present invention to provide a distal targeting system having a handheld location pad which provides an operator-perceptible indication of the relative displacement and directional alignment of a guide for a drill or other surgical instrument with respect to a bore of an orthopedic appliance.

It is yet another object of some aspects of the present invention to provide a distal targeting system having a handheld location pad which provides an operator-perceptible indication of the position and directional alignment of a guide for a surgical instrument with respect to a bore of an orthopedic appliance.

These and other objects of the present invention are attained by a distal targeting system, wherein a hand-held location pad is integral with a guide section for a drill or similar surgical instrument. The system employs magnetic field generators and magnetic field sensors, which can be wired or wireless. Either a sensor or a generator is disposed in an orthopedic appliance, such as an intramedullary nail. The sensor is capable of detecting and discriminating the strength and direction of a magnetic field. Control circuitry, preferably located in the location pad is responsive to a signal of the sensor, and determines the displacement and relative directions of an axis of the guide section and a bore in the orthopedic appliance. A screen display and optional speaker in the location pad provide an operator-perceptible indication that enables the operator to adjust the position of the guide section so as to align its position and direction with the bore.

The invention provides a distal targeting system for determining the location and orientation of an instrument relative to a target, including a movable guide assembly for guiding the instrument toward the target, a plurality of field generators in the guide assembly that generate known distinguishable fields in response to drive signals, and one or more sensors disposed at known locations with respect to the target that generate sensor signals in response to the fields. The sensors have known alignments with an axis of the target. The system includes a signal processor responsive to the drive signals and the sensor signals for producing three location coordinates of a point on the guide assembly, and two orientation coordinates of an axis of the guide assembly. The system includes a display responsive to the signal processor that provides an indication of a location of the point with respect to the target and of an alignment between the axis of the guide assembly and the axis of the target.

According to an aspect of the distal targeting system, the display is integral with the guide assembly.

According to a further aspect of the distal targeting system, the display includes a ball-and-crosshairs indication.

According to one aspect of the distal targeting system, the sensors are wireless sensors.

One aspect of the distal targeting system includes a control unit, and a plurality of external field generators responsive to control signals of the control unit, wherein external fields generated by the external field generators provide power to the sensors.

According to still another aspect of the distal targeting system, the external fields further provide the drive signals to the field generators in the guide assembly.

According to another aspect of the distal targeting system, the indication includes five positional and orientation coordinates.

According to a further aspect of the distal targeting system, the target is a hollow appliance, and the sensors are insertable therein.

According to yet another aspect of the distal targeting system, the target is an intramedullary nail.

According to one aspect of the distal targeting system, the sensors are integral with the target.

Still another aspect of the distal targeting system includes a plurality of locating elements having location field detectors therein. The locating elements are disposed at known locations with respect to a fixed frame of reference. The signal processor is responsive to the locating elements to determine a corrected indication of the location of the point.

The invention provides a distal targeting system for determining the location and orientation of an instrument relative to a target, including a movable guide assembly for guiding an instrument toward a target, a plurality of field generators in the guide assembly that generate known distinguishable fields in response to drive signals, and one or more sensors disposed at known locations with respect to the target that generate sensor signals in response to the fields. The sensors have known alignments with an axis of the target. The system includes a signal processor responsive to the drive signals and the sensor signals for producing three location coordinates of a point on the guide assembly and two orientation coordinates of an axis of the guide assembly. The system includes a location pad attached to the guide assembly and moveable therewith, responsive to the signal processor that provides a quantitative indication of a distance and a location of the point with respect to the target and of an alignment between the axis of the guide assembly and the axis of the target.

According to an aspect of the distal targeting system, the sensors are wireless sensors.

Still another aspect of the distal targeting system includes a control unit, and a plurality of external field generators responsive to control signals of the control unit, wherein external fields generated by the external field generators provide power to the sensors.

According to an additional aspect of the distal targeting system, the external fields further provide the drive signals to the field generators in the guide assembly.

According to one aspect of the distal targeting system, the quantitative indication includes five positional and orientation coordinates.

According to another aspect of the distal targeting system, the target is a hollow appliance, and the sensors are insertable therein.

According to a further aspect of the distal targeting system, the appliance is an intramedullary nail.

According to yet another aspect of the distal targeting system, the sensors are integral with the target.

An additional aspect of the distal targeting system includes a plurality of locating elements having location field detectors therein. The locating elements are disposed at known locations with respect to a fixed frame of reference. The signal processor is responsive to the locating elements to determine a corrected indication of the location of the point.

The invention provides a distal targeting system for determining the location and orientation of an instrument relative to a target, including a hand-held movable guide assembly for guiding an instrument toward a target, a plurality of field generators in the guide assembly that generate known distinguishable fields in response to drive signals, a plurality of sensors disposed at known locations with respect to the target that generate sensor signals in response to the fields, the sensors has known alignments with an axis of the target, a signal processor disposed in the guide assembly responsive to the drive signals and the sensor signals for producing three location coordinates of a point on the guide assembly and two orientation coordinates of an axis of the guide assembly, and a location pad disposed in the guide assembly, responsive to the signal processor that provides a quantitative indication of a distance and a location of the point with respect to the target and of an alignment between the axis of the guide assembly and the axis of the target, the location pad has a visual display for providing the quantitative indication.

According to an aspect of the distal targeting system, the display is integral with the guide assembly.

According to yet another aspect of the distal targeting system, the display includes a ball-and-crosshairs indication.

According to a further aspect of the distal targeting system, the sensors are wireless sensors.

According to one aspect of the distal targeting system, the visual display further provides a qualitative indication of a misalignment between the axis of the guide assembly and the axis of the target.

An additional aspect of the distal targeting system includes a control unit, and a plurality of external field generators responsive to control signals of the control unit, wherein external fields generated by the external field generators provide power to the sensors.

The invention provides a distal targeting system for determining the location and orientation of an instrument relative to a target, including a movable guide assembly for guiding an instrument toward a target, a plurality of field generators in the guide assembly that generate known distinguishable fields in response to drive signals, one or more sensors disposed at known locations with respect to the target that generate sensor signals in response to the fields. The sensors have known alignments with an axis of the target, a signal processor disposed in the guide assembly responsive to the drive signals and the sensor signals has a first output responsive to a difference between a location of the target and a location of the guide assembly and second output responsive to a difference between a direction of an axis of the guide assembly and a direction of the axis of the target, and a display disposed in the guide assembly responsive to the signal processor that provides a qualitative indication of the first output and the second output.

According to an aspect of the distal targeting system, the display is integral with the guide assembly.

According to still another aspect of the distal targeting system, the display includes a ball-and-crosshairs indication.

The invention provides a distal targeting system for determining the location and orientation of an instrument relative to a target, including a movable guide assembly for guiding an instrument toward a target, a magnet disposed at a known location with respect to the target that has a known alignment with an axis of the target, a plurality of field detectors in the guide assembly producing field detector signals responsive to a field of the magnet. A signal processor disposed in the guide assembly responsive to the field detector signals has outputs representative of a difference between a location of the target and a location of the guide assembly and a difference between a direction of an axis of the guide assembly and a direction of the axis of the target. The system includes a display disposed in the guide assembly responsive to the signal processor that provides a first indication of the difference between the location of the target and a second indication of the difference between the direction of the axis of the guide assembly.

The invention provides a distal targeting system for determining the location and orientation of an instrument relative to a target, including a movable guide assembly for guiding the instrument toward the target. The system includes one or more first field elements in the guide assembly, and one or more second field elements disposed at known locations with respect to the target. The first field elements and the second field elements are either sensors or field generators, at least one of the first field elements and the second field elements being sensors. The field generators produce known distinguishable fields in response to drive signals, and the sensors produce sensor signals in response to the fields. The sensors have known alignments with an axis of the target. The system includes one or more third field elements, wherein the third field elements are field generators. The system includes a signal processor responsive to the drive signals and the sensor signals for producing three location coordinates of a point on the guide assembly and two orientation coordinates of an axis of the guide assembly. The system includes a display responsive to the signal processor that provides an indication of a location of the point with respect to the target and of an alignment between the axis of the guide assembly and the axis of the target.

According to an aspect of the distal targeting system, the first field elements are the field generators, and the second field elements are sensors. The second field elements are responsive to distinguishable fields of the first field elements and the third field elements.

According to yet another aspect of the distal targeting system, the first field elements are the sensors, and the second field elements are the field generators. The first field elements are responsive to distinguishable fields of the second field elements and the third field elements.

According to an additional aspect of the distal targeting system, the first field elements and the second field elements are the sensors.

According to one aspect of the distal targeting system, the first field elements and the second field elements are wireless and powered by fields of the third field elements.

According to an additional aspect of the distal targeting system, the display is integral with the guide assembly.

According to one aspect of the distal targeting system, the display includes a ball-and-crosshairs indication.

According to another aspect of the distal targeting system, the sensors are wireless sensors.

According to a further aspect of the distal targeting system, the indication includes five positional and orientation coordinates.

According to yet another aspect of the distal targeting system, the target is a hollow appliance, and the sensors are insertable therein.

According to still another aspect of the distal targeting system, the target is an intramedullary nail.

According to an additional aspect of the distal targeting system, the sensors are integral with the target.

Another aspect of the distal targeting system includes a plurality of locating elements having location field detectors therein. The locating elements are disposed at known locations with respect to a fixed frame of reference, wherein the signal processor is responsive to the locating elements to determine a corrected indication of the location of the point.

The invention provides a method for determining the location and orientation of an instrument relative to a target, including generating one or more distinguishable fields, sensing a strength and an orientation of each of the fields at known locations with respect to the target, providing a movable hand-held guide assembly for directing the instrument to the target, and providing a display on the assembly. The display indicates a location of a point of the assembly relative to the target and of an alignment between an axis of the assembly and an axis of the target. After sensing, the method includes calculating three location coordinates of the point relative to the target.

According to an aspect of the method, the display indicates the location of the point using a ball-and-crosshairs indication.

In still another aspect of the method, sensing is performed using wireless sensors.

According to one aspect of the method, the target is a hollow appliance, and the wireless sensors are insertable therein.

According to another aspect of the method, the target is an intramedullary nail.

According to a further aspect of the method, the wireless sensors are integral with the target.

According to an additional aspect of the method, the display indicates five positional and orientation coordinates.

In still another aspect of the method, the fields are generated in a proximity of the target, and sensing is performed remote from the target.

In an additional aspect of the method, the fields are generated remote from the target, and sensing is performed in a proximity of the target.

BRIEF DESCRIPTION OF THE DRAWINGS

For a better understanding of these and other objects of the present invention, reference is made to the detailed description of the invention, by way of example, which is to be read in conjunction with the following drawings, wherein.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances well-known circuits, control logic, and the details of computer program instructions for conventional algorithms and processes have not been shown in detail in order not to unnecessarily obscure the present invention.

FIRST EMBODIMENT

Figure 1:
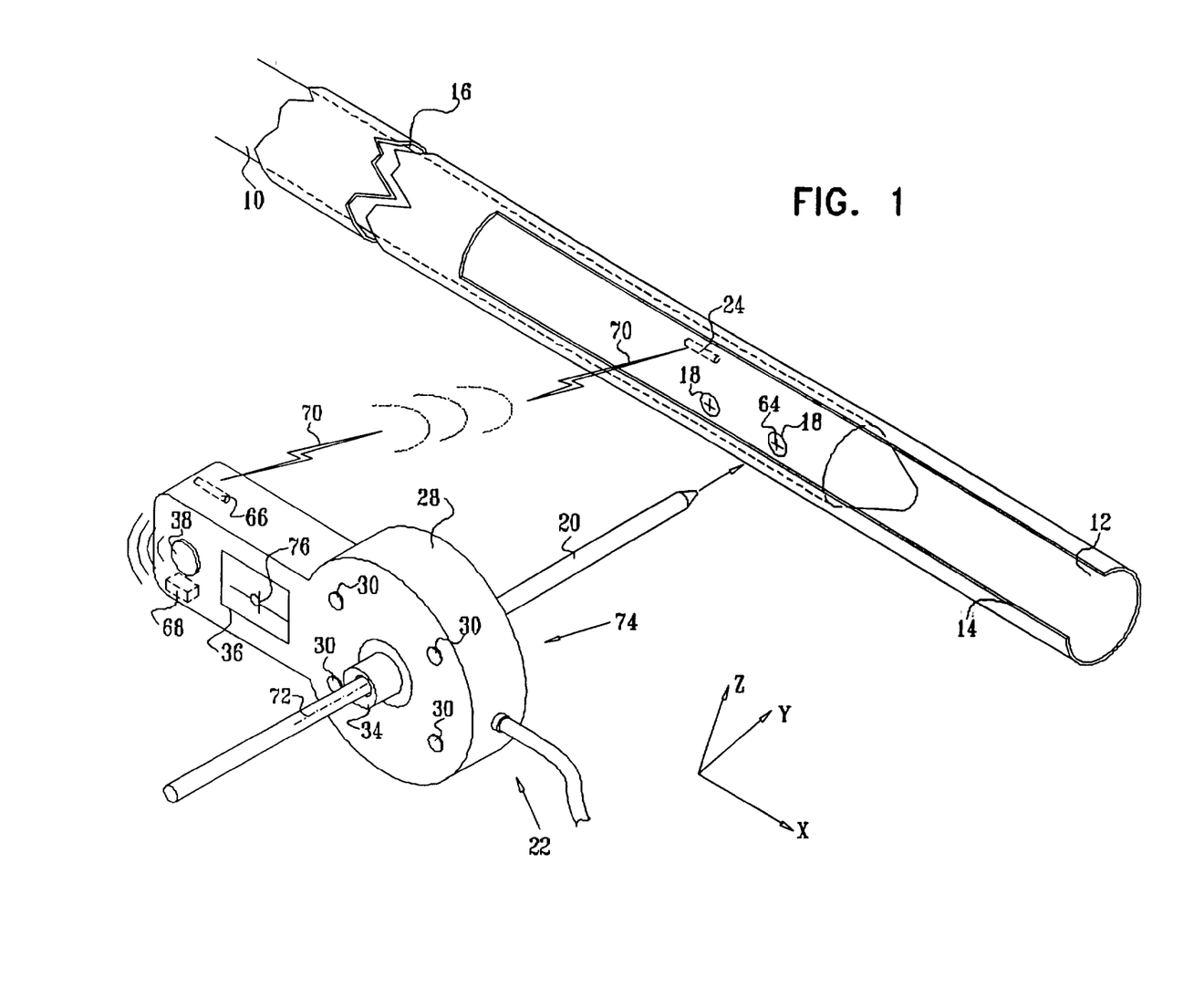
FIG. 1 is a schematic illustration of a distal targeting system which is constructed and operative in accordance with a preferred embodiment of the invention.

Turning now to the drawings, reference is made to FIG. 1, which is a schematic illustration of a distal targeting system which is constructed and operative in accordance with a preferred embodiment of the invention. A hollow appliance, preferably an intramedullary nail 10, is suitably dimensioned to a medullary cavity 12 of a bone 14 for the purpose of stabilizing a fracture 16. The intramedullary nail 10 is provided with at least one bore 18 for receiving a locking member 20 therethrough. The locking member 20 is typically realized as a wire or set screw, and must be inserted by the operator without benefit of direct visualization of the bore 18.

A magnetic field positioning arrangement 22 enables the operator to localize the bore 18 and to align the locking member 20 with the bore 18 prior to insertion therein. A miniature magnetic sensor 24 is disposed in the intramedullary nail 10, at known positional and rotational offsets from a principal axis 64 of the bore 18. In a preferred embodiment of the invention, the sensor 24 is a magnetic field receiver, which is sensitive to the presence of a magnetic field and to the orientation of flux lines of the magnetic field. The sensor 24 is preferably a miniature sensor such as is disclosed in the patent documents U.S. Pat. No. 5,913,820 to Bladen et al. or WO 96/05768 to Ben-Haim et al., which are herein incorporated by reference.

Preferably the sensor 24 is slidably insertable into the intramedullary nail 10, and may be optionally removed following completion of the surgical procedure. Alternatively, the sensor 24 can be integral with the intramedullary nail 10.

It is preferred that the sensor 24 be an independent, wireless unit, powered by energy radiated from outside the patient's body. The sensor 24 is provided with a plurality of wireless transponders, details of which are disclosed hereinbelow. A location pad 28 is provided with an antenna 66, and with a control unit 68 having driving and receiving circuitry, which are adapted to exchange wireless signals 70 with the sensor 24, the output of the sensor 24 being responsive to the strength and orientation of an externally-applied magnetic field flux. A principal axis 72 of a guide section 74 of the location pad 28 is indicated by an "x" in FIG. 1. The location pad 28 is preferably affixed to a guide section 74, which is disclosed in further detail below.

To minimize interference with the operation of the magnetic field positioning arrangement 22, the intramedullary nail 10 is preferably composed of a suitable non-interfering material, for example titanium. However, as will be apparent from the disclosure hereinbelow, even magnetically-responsive nails can be accommodated using the teachings of the present invention.

In a preferred embodiment, the handheld location pad 28 has a plurality of magnetic field generator modules 30, typically comprising coils, each operating at a different frequency or at a different time. Preferably, there are four magnetic field generator modules 30. Additionally, an aperture 34 of location pad 28 is provided for insertion of the locking member 20 therethrough. The sensor 24 is powered by wireless power transmission from the antenna 66 of the location pad 28.

The control unit 68 allows the determination of the positions and directional orientations of the sensor 24 relative to each of the field generator modules 30. Then, the relative position of the aperture 20 of the location pad 28 and hence the locking member 20 with respect to the bore 18 can be calculated.

Readouts, responsive to the calculation of the relative positions of location pad 28 and the sensor 24, are displayed on a screen display 36. Using feedback provided by the screen display 36, the sensor 24 can be accurately localized. Localization of the sensor 24 enables the position of the bore 18 to be accurately determined, by making appropriate adjustments for the offsets between the bore 18 and the sensor 24. Directional alignment of the location pad 28 with the bore 18 is also determined, as the sensor 24 is sensitive to the directional orientation of the magnetic fields that are produced by the magnetic field generator modules 30.

The screen display 36 and the guide section 74 are both integral in the location pad 28. The screen display 36 provides a real-time visual indication of the amount and the nature of any misalignment, preferably by means of a ball-and-crosshairs display 76. Many other operator-perceptible indicators of positional and angular alignment can also be employed. The location pad 28 is also provided with audio circuitry and a small loudspeaker 38 which provides an audible indication of the current misalignment in real-time. Alternatively or additionally, the screen display 36 can be realized as a computer monitor connected to a computer or directly to the control unit 68.

Figure 2:
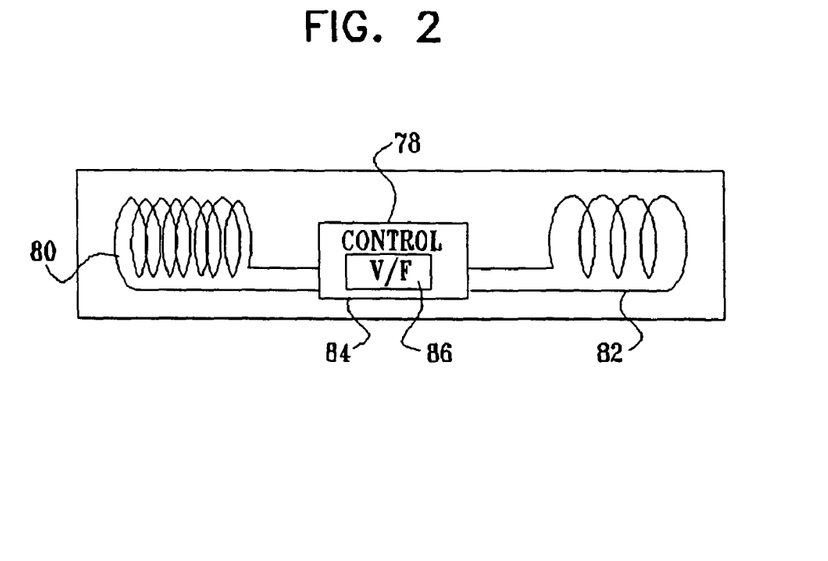
FIG. 2 illustrates a transponder of a sensor of the distal targeting system shown in FIG. 1.

Reference is now made to FIG. 2, which schematically shows details of a transponder 78, which is a component of the sensor 24 (FIG. 1) in accordance with a preferred embodiment of the invention. As shown in FIG. 2, the transponder 78 comprises a power coil 80 and a sensing coil 82, coupled to a control chip 84. Preferably, the chip 84 includes a voltage-to-frequency (V/F) converter 86, which generates a RF signal, the frequency of which is proportional to the voltage produced by current through the sensor coil 82 flowing across a load (not shown). The power coil 80 is preferably optimized to receive and transmit high-frequency signals, in the range above 1 MHz. The sensor coil 82, on the other hand, is preferably designed for operation in the range of 1–3 kHz, the frequencies at which the magnetic field generation modules 30 (FIG. 1) generate their electromagnetic fields. Alternatively, other frequency ranges may be used, as dictated by application requirements. The entire transponder 78 is typically 2–5 mm in length and 2–3 mm in outer diameter, enabling it to fit conveniently inside the intramedullary nail 10 (FIG. 1).

Figure 3:
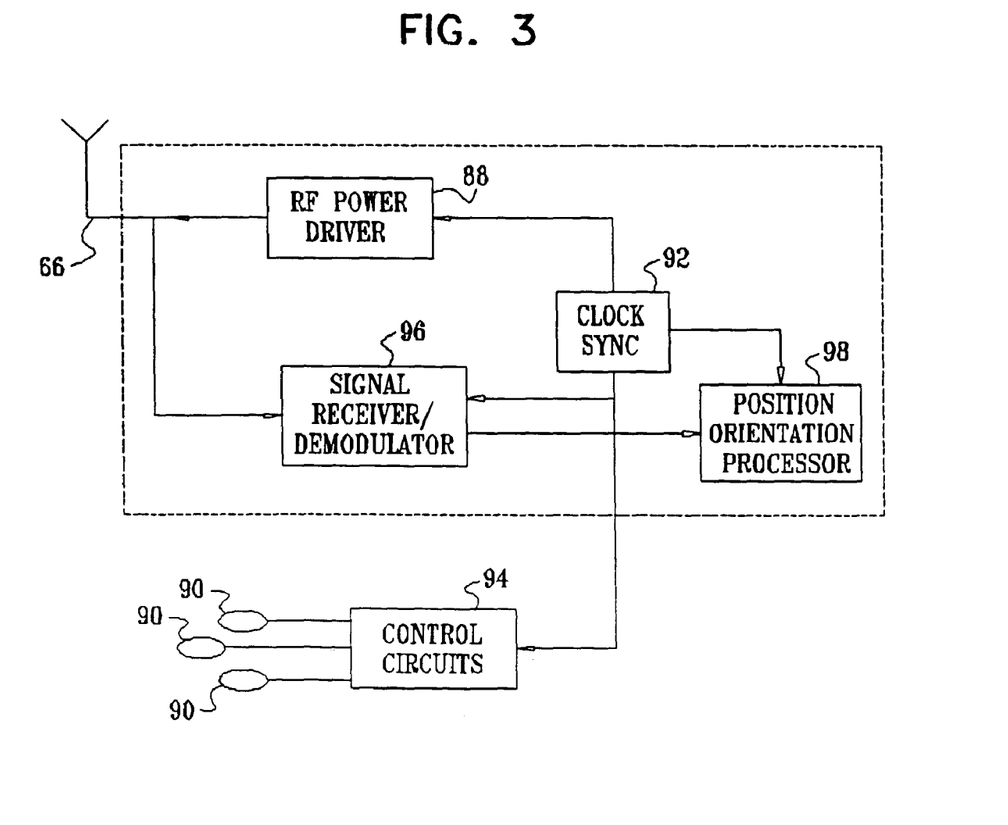
FIG. 3 is a schematic block diagram of driving and processing circuits of the transponder shown in FIG. 2.

Reference is now made to FIG. 3, which schematically shows driving and processing circuits for the transponder 78 (FIG. 2) in accordance with a preferred embodiment of the invention. This circuitry is preferably integral with the location pad 28 (FIG. 1) and is typically included in the control unit 68. In some embodiments, the circuitry may be external to the location pad 28. The location pad 28 includes a RF power driver 88, which drives the antenna 66 to emit a power signal, preferably in the 2–10 MHz range. The power signal causes a current to flow in the power coil 80, which is rectified by the chip 84 and used to power its internal circuits. Meanwhile, the electromagnetic fields produced by the magnetic field generator modules 30 (FIG. 1), here embodied as generator coils 90, cause a current to flow in the sensor coil 82. This current has frequency components at the same frequencies as the driving currents flowing through the generator coils. The current components are proportional to the strengths of the components of the respective magnetic fields produced by the field generator coils 90 in a direction parallel to the sensor coil axis. Thus, the amplitudes of the currents indicate the position and orientation of the sensor coil 82 relative to the field generator coils 90.

Preferably, a clock synchronizer 92 is used to synchronize control circuits 94 and the driver 88, which can be disposed either integral with or external to the location pad 28, as is disclosed further herein. Most preferably, the frequency of the RF driving signal produced by the driver 88 is set to be an integer multiple of the magnetic field frequencies of the magnetic field generator coils 90 (FIG. 1). The clock synchronization enables the chip 84 (FIG. 2) to use phase-sensitive detection in order to enhance the signal/noise ratio of the signal from the sensor coil 82. The phase of the sensor signals is preferably also used to resolve ambiguity that would otherwise occur in the signals under 180° reversal of the axis of the sensor coil 82.

Referring again to FIG. 2, the chip 84 measures the currents flowing in sensor coil 82 at the different field frequencies. It encodes this measurement in a high-frequency signal, which it then transmits back via the power coil 80 to the antenna 66. Preferably, the RF signal produced by the chip 84 has a carrier frequency in the 50–150 MHz range. The RF signal produced in this manner is modulated with three different frequency modulation (FM) components that vary over time at the respective frequencies of the fields generated by the field generator coils 90 (FIG. 3). The magnitude of the modulation is proportional to the current components at the three frequencies. An advantage of using frequency modulation, rather than amplitude modulation, to convey the amplitude measurements of the sensor coil 82 from the transponder 78 to the antenna 66 is that the information in the signal is unaffected by the variable attenuation of the body tissues through which the signal must pass.

Alternatively, the chip 84 may comprise a sampling circuit and analog/digital (A/D) converter (not shown), which digitizes the amplitude of the current flowing in the sensor coil 82. In this case, the chip 84 generates a digitally modulated signal, and RF-modulates the signal for transmission by the power coil 80. Any suitable method of digital encoding and modulation may be used for this purpose. Other methods of signal processing and modulation will be apparent to those skilled in the art.

The frequency modulated or digitally modulated signal transmitted by the power coil 80 is picked up by a receiver 96, coupled to the antenna 66. The receiver 96 demodulates the signal to generate a suitable input to a position and orientation processor 98. Typically, the receiver 96 amplifies, filters and digitizes the signals 70 (FIG. 1) from the transponder 78. The digitized signals are received and used by the position and orientation processor 98 to derive the position and orientation of the bore 18 (FIG. 1) from a computation of the position and orientation of the transponder 78. The position and orientation of the transponder 78 is determined relative to the field generator coils 90. Since the field generator coils 90 are in known positions and orientations relative to the bore 18, the position and orientation of the bore 18 can readily be determined. Typically, the position and orientation processor 98 can be realized as a general-purpose computer (not shown) or as an embedded microprocessor in the control unit 68 (FIG. 1), which is programmed and equipped with appropriate input circuitry for processing the signals from the receiver 96. The information derived by the position and orientation processor 98 is used to generate an image on the screen display 36 (FIG. 1), for example, or to provide other diagnostic information or guidance to the operator.

Figure 4:
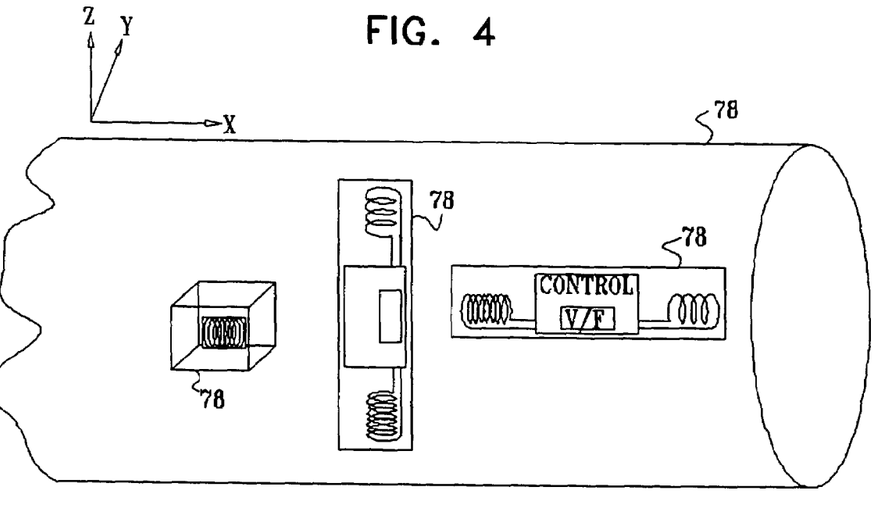
FIG. 4 is an enlarged fragmentary schematic view of a sensor used in the distal targeting system shown in FIG. 1.

Reference is now made to FIG. 1 and to FIG. 4, which is an enlarged fragmentary schematic view of the sensor 24 (FIG. 1), in accordance with a preferred embodiment of the present invention. In this embodiment, three identical copies of the transponder 78 are disposed within the sensor 24, and are preferably mutually orthogonal, as indicated by the coordinate axes in FIG. 4. It is thus possible for six positional and orientation coordinates to be unambiguously identified, in accordance with the algorithms disclosed in the International Patent Publication WO 94/04938, which is incorporated herein by reference. These coordinates include the X, Y, Z coordinates of a predetermined point on the guide section 74, and the angles between the principal axis 64 and the principal axis 72 in the XY, YZ and XZ planes. Alternatively, the sensor 24 may comprise only a single transponder 78, which is sufficient (together with multiple field generator coils 90 to determine the X, Y, Z coordinates and the angles between the principal axis 64 and the principal axis 72 in the YZ and XZ planes.

Further details of the sensor 24 are disclosed in application Ser. No. 10/029,473 entitled, "Wireless Position Sensor," filed Dec. 21, 2001, which is assigned to the assignee of the present patent application and is incorporated herein by reference.

Referring again to FIG. 1 and FIG. 3, the position and orientation processor 98, using the algorithms disclosed in the above-noted patent documents WO 96/05768 and WO 94/04938, and the information received from the sensor 24, determines the relative displacement between the bore 18 and the aperture 34 on the location pad 28, and the angular deviation between the principal axis 64 of the bore 18 and the principal axis 72 of the guide section 74. Readouts and visual displays are provided on the screen display 36. The readouts may provide a quantitative measure of both the linear displacement and angular deviations between the principal axes.

Figure 5:
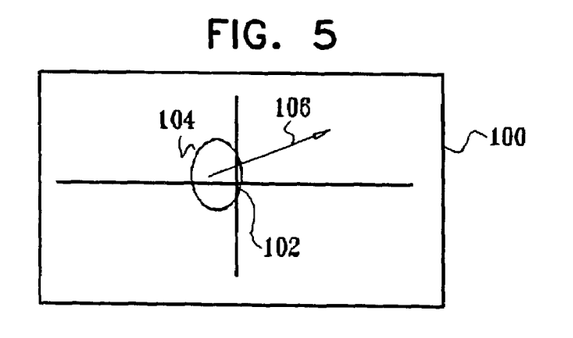
FIG. 5 is an exemplary screen of a screen display of the distal targeting system shown in FIG. 1.

Reference is now made to FIG. 1 and FIG. 5. FIG. 5 is an exemplary screen 100, which is displayed on the screen display 36 (FIG. 1). A cross-hair intersection 102 represents the location of the bore 18 (FIG. 1), or another target. The location of a circle 104 represents the linear displacement of the principal axis 72 of the guide section 74 relative to the principal axis 64 of the bore 18. A closing vector 106 provides an operator-perceptible indication of angular misalignment, between vectors representing the two principal axes. The non-zero magnitude of the vector 106 in FIG. 5 indicates an actual angular misalignment between the guide section 74 and the bore 18. It is also possible to further represent components of a difference vector between the two principal axes in the XY, XZ, and YZ planes.

Figure 6:
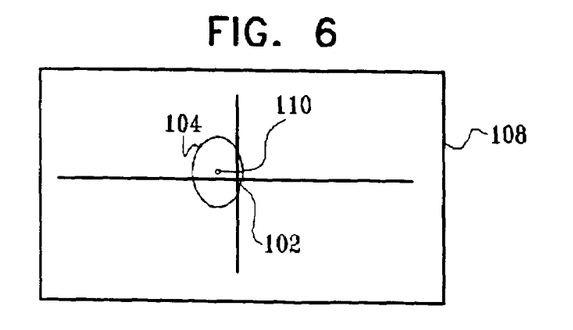
FIG. 6 is another exemplary screen of a screen display similar to FIG. 5.

Reference is now made to FIG. 1 and FIG. 6, which is another screen 108, similar to the screen 100, wherein like elements are given like reference numerals. When compared to the screen 100, the screen 108 indicates that linear displacement of the principal axis 72 of the guide section 74 and the principal axis 64 of the bore 18 is unchanged. However the guide section 74 has been rotated, such that the principal axes are parallel. The vector 106 (FIG. 5) is now perpendicular to the screen 108, and appears simply as a point 110.

Operation

To use the magnetic field positioning arrangement 22, all required surgical incisions, creation of an entry portal in the bone 14, and preparation of the medullary cavity 12 are first accomplished by the operator using conventional invasive technique or minimally invasive technique as appropriate. The intramedullary nail 10 is introduced into the medullary cavity 12 across the fracture 16. Care is preferably taken to remove magnetically interfering objects from the operative field, although techniques for achieving metal immunity may also be used, as described above. The operator enters any required offset information into the location pad 28, places the location pad 28 at an estimated position of the bore 18, and aims the aperture 34 in the general direction of the bore 18. The sensor 24 and the magnetic field generator modules 30 are energized. Audiovisual indications provided by the screen display 36 and the loudspeaker 38 are then exploited by the operator to optimize the position and orientation of the location pad 28. When an optimum alignment has been achieved, the location pad 28 is held in position, and a hole is drilled through the cortex of the bone 14, preferably using the aperture 34 of the location pad 28 as a drill guide. The locking member 20 is inserted and emplaced in the bore 18. The location pad 28 is thereafter disengaged from the locking member 20 and removed from the operative field. The surgical operation is then completed routinely.

The sensor 24 used in this and following embodiments may similarly be mounted on an insertable probe rather than being permanently implanted in the nail 10, so long as the position of the sensor 24 relative to the bore 18 is known.

SECOND EMBODIMENT

Figure 7:
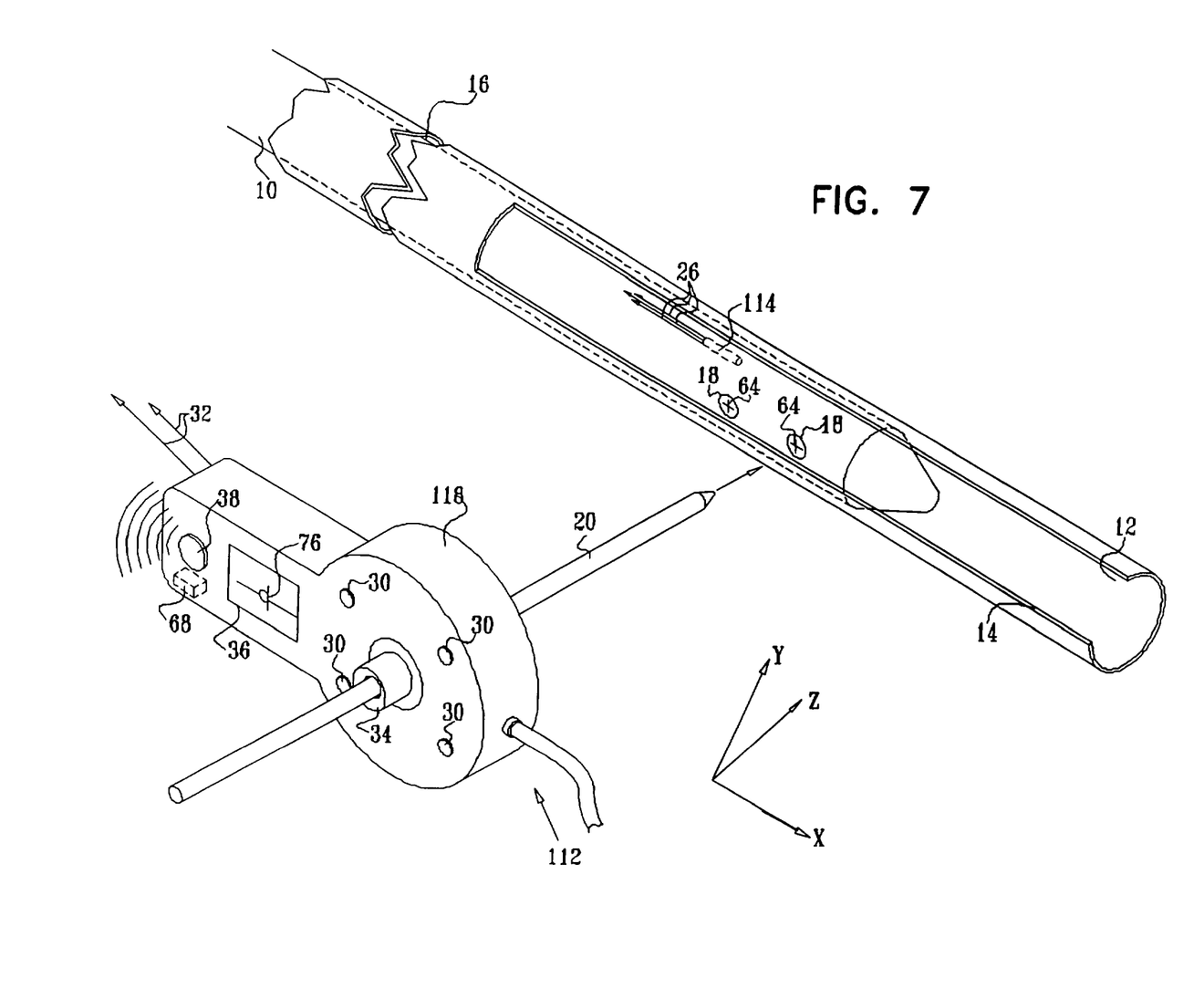
FIG. 7 is a schematic illustration of a distal targeting system which is constructed and operative in accordance with an alternate embodiment of the invention, in which a sensor therein is powered by electrical leads.

Reference is now made to FIG. 7, which is a schematic illustration of a distal targeting system which is constructed and operative in accordance with an alternate embodiment of the invention. Elements in FIG. 7 that are identical to those of FIG. 1 are given like reference numerals. In this embodiment, a magnetic field positioning arrangement 112 has a wired magnetic sensor 114, in place of the wireless sensor 24 (FIG. 1). Leads 26 are provided for powering the sensor 114 and obtaining a readout or other data therefrom. Leads 32 are provided to carry signals to a location pad 118 from the sensor 114. The location pad 118 is similar to the location pad 28 (FIG. 1), except that the location pad 118 requires no antenna or wireless receiving circuitry.

Figure 8:
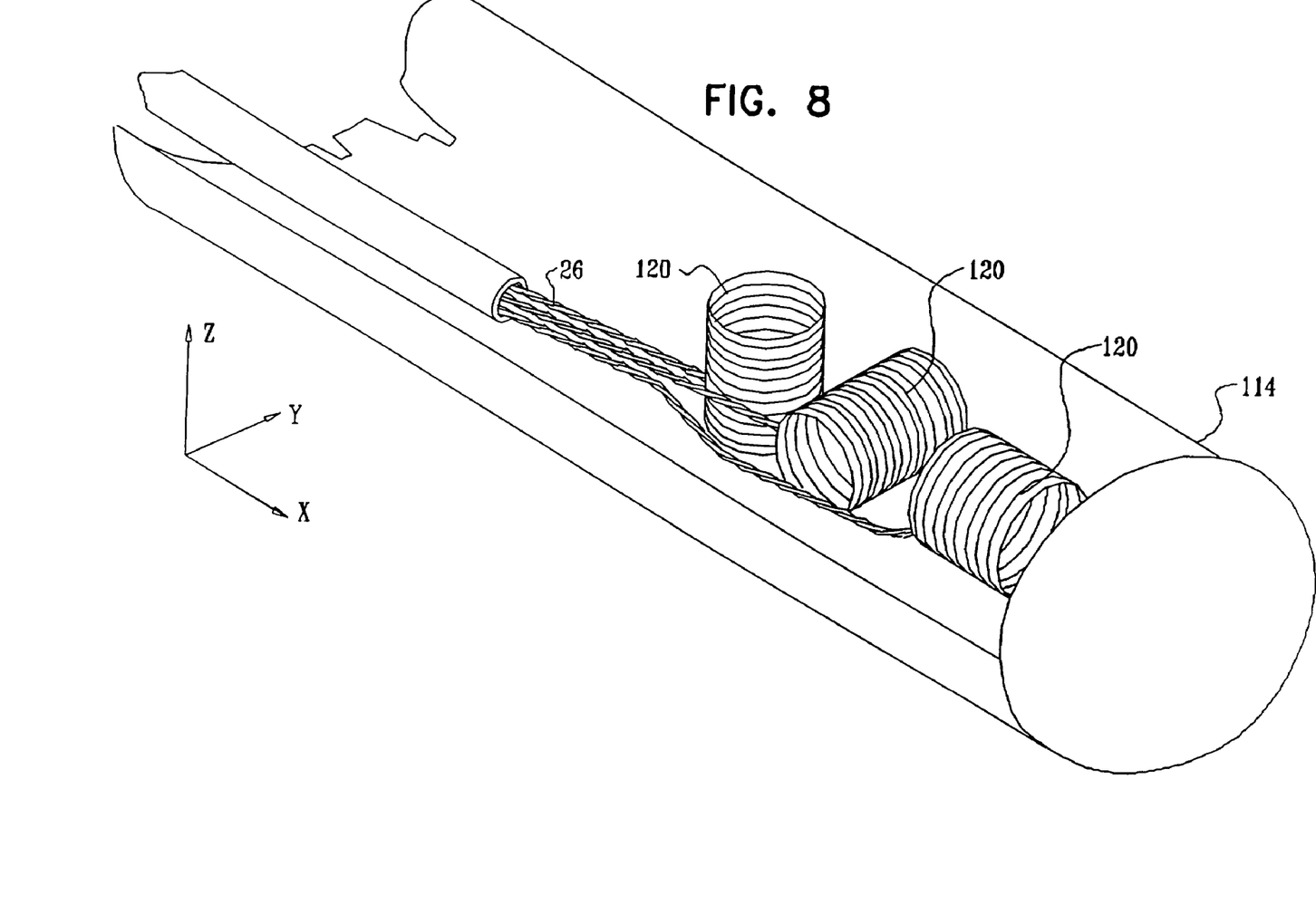
FIG. 8 is an enlarged fragmentary schematic view of a sensor used in the distal targeting system shown in FIG. 7.

Reference is now made to FIG. 8, which is an enlarged fragmentary schematic view of the sensor 114 (FIG. 7). Three identical sensor coils 120, which can be wound on air cores or magnetic cores, are disposed within the sensor 114, and are preferably mutually orthogonal, as indicated by the coordinate axes in FIG. 8. The leads 26 are preferably twisted pairs, and can be electrically shielded to reduce stray pickup. Operation of the sensor 114 is otherwise similar to that of the sensor 24 (FIG. 1). Further details of the sensor 114 are disclosed in the above-noted patent document WO 96/05768.

THIRD EMBODIMENT

Figure 9:
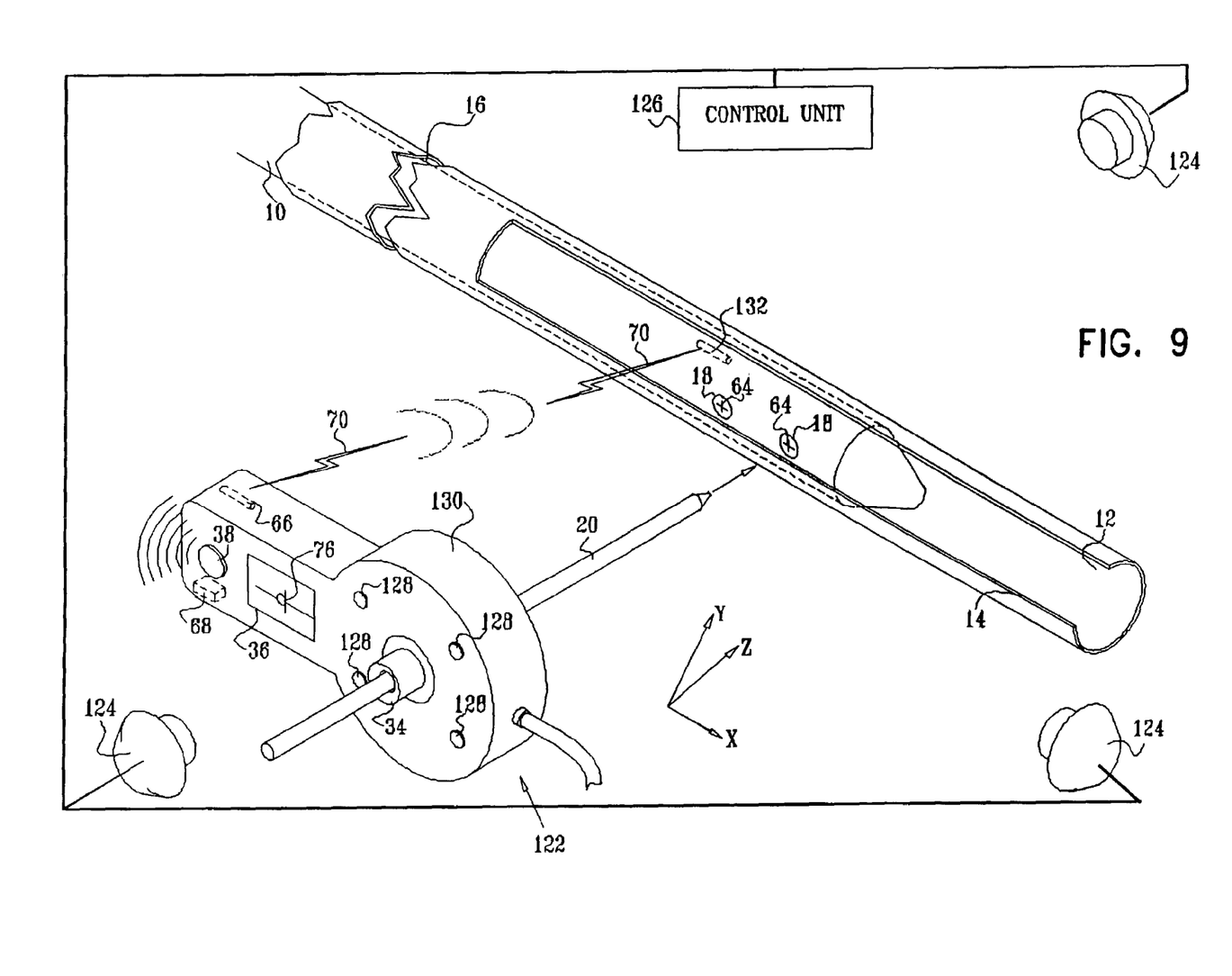
FIG. 9 is a schematic illustration of a distal targeting system which is constructed and operative in accordance with an alternate embodiment of the invention, wherein a sensor and magnetic field modules are powered by wireless power transmission from external field generators.

Reference is now made to FIG. 9, which is a schematic illustration of a distal targeting system which is constructed and operative in accordance with an alternate embodiment of the invention. Elements in FIG. 9 that are identical to those of FIG. 1 are given like reference numerals. A magnetic field positioning arrangement 122 is similar to the magnetic field positioning arrangement 22 (FIG. 1), except now, there are three or more external field generators 124, driven by a control unit 126. The field generators 124 are preferably fixed to the operating table or to another non-moving fixture, and provide an absolute frame of reference. Using this embodiment, an absolute position of the sensor can be obtained. As is explained in further detail below, different variations of this embodiment are possible. It is possible to exchange the roles of the sensor and the magnetic field generator modules. Thus in one variation, magnetic field generator modules and sensor can be located as in the embodiment of FIG. 1. In another variation, the magnetic field can be generated from within or in the proximity of the intramedullary nail, and a plurality of sensors can be disposed in the location pad.

The magnetic field positioning arrangement 122 features a plurality of wireless magnetic field elements 128 in a location pad 130. A miniature magnetic field element 132 is disposed in the intramedullary nail 10, at known positional and rotational offsets from a principal axis 64 of the bore 18. In one variation, the field elements 128 are magnetic field generating elements, and the field element 132 is a sensor. In another variation the field elements 128 are sensors and the field element 132 is a magnetic field generating element.

In a further variation both the field elements 128 and the field element 132 are sensors, all of which sense magnetic fields that are generated by the field generators 124.

In further variations, some or all of the field elements 128 and the field element 132 are powered by intense, high frequency magnetic fields generated by the field generators 124, in which case some or all of the field elements 128 and the field element 132 can be wireless. A further advantage of this embodiment is the reduction to a minimum of the size and weight of the circuitry required in the location pad 130.

FOURTH EMBODIMENT

Figure 10:
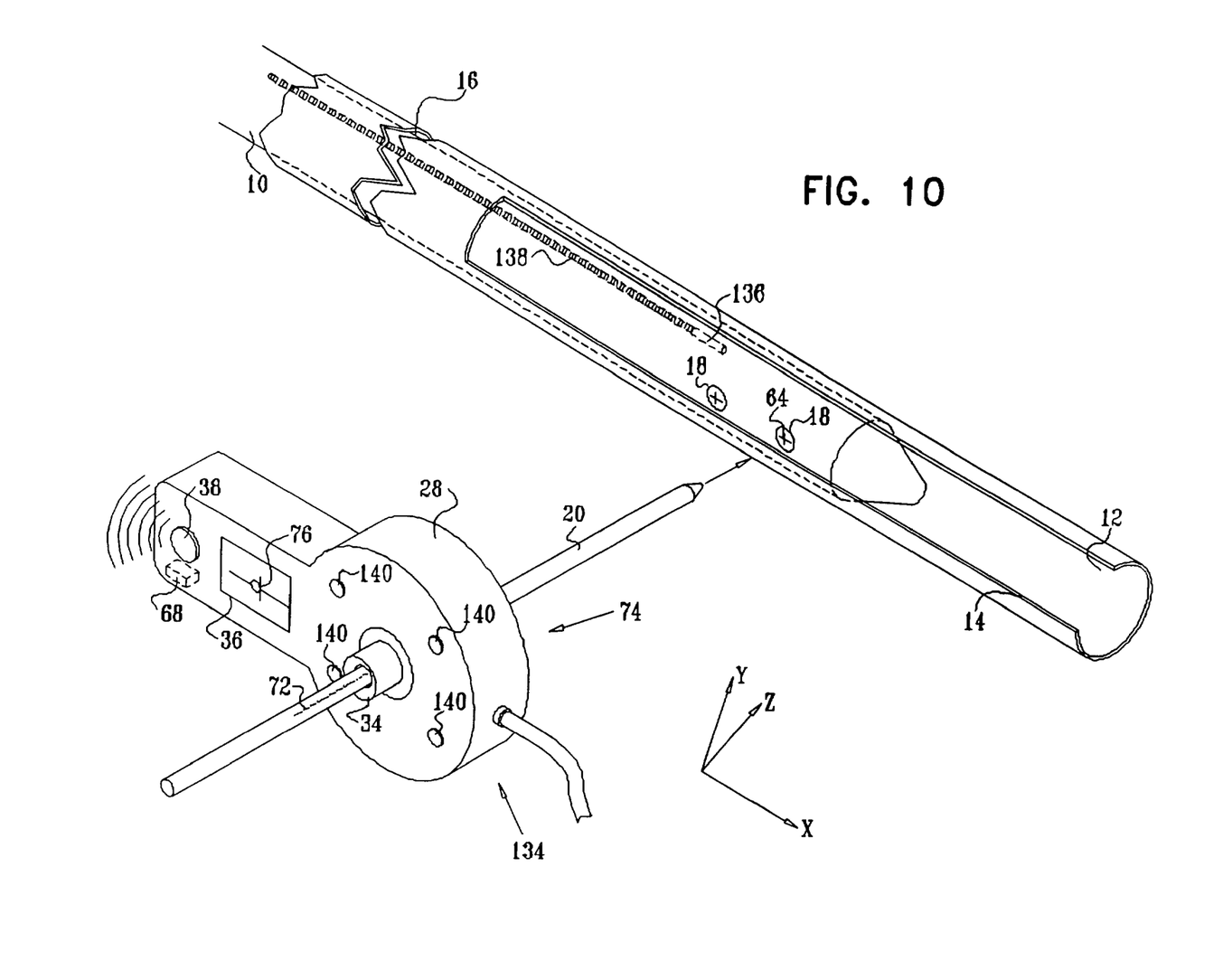
FIG. 10 is a schematic illustration of a distal targeting system which is constructed and operative in accordance with an alternate embodiment of the invention, wherein a permanent magnet is used in place of a sensor.

Reference is now made to FIG. 10, which is a schematic illustration of a distal targeting system which is constructed and operative in accordance with an alternate embodiment of the invention. Elements in FIG. 10 that are identical to those of FIG. 1 are given like reference numerals. A magnetic field positioning arrangement 134 is similar to the magnetic field positioning arrangement 22 (FIG. 1). However, a permanent magnet 136 now replaces the sensor 24 within the intramedullary nail 10. The magnet 136 can be 1.5–2 mm. OD by 5 mm long. NB45 magnets are suitable. The magnet 136 can be permanently emplaced in the intramedullary nail 10, but preferably is insertable therein by attaching the magnet 136 to a calibrated probe 138 having a suitable mechanical stop (not shown). When the probe 138 is inserted into the intramedullary nail 10, the operative position of the magnet 136 is at a known location with respect to the bore 18.

Four magnetic field detectors 140 are incorporated in a location pad 142, which is generally similar to the location pad 28 (FIG. 1). The field detectors 140 detect the field strength and orientation of the magnetic field of the magnet 136. Signal processing circuitry, preferably located in the control unit 68, is coupled to the field detectors 140. Using the algorithms and techniques disclosed in the above-noted international Patent Publication WO 94/04938, the disposition of the location pad 142 with respect to the bore 18 and the angular misalignment between the principal axis 72 and the principal axis 64 can be determined and displayed on the screen display 36, as a quantitative or a qualitative indication as disclosed hereinabove.

FIFTH EMBODIMENT

When a metal or other magnetically-responsive article is brought into the vicinity of the target being tracked, or if the target itself, such as the nail 10, is magnetically responsive, the magnetic fields in the vicinity of the target are distorted, due to eddy currents that produce parasitic magnetic fields. Such parasitic fields and other types of distortion can lead to errors in determining the position of the object being tracked. Whereas, in the above-noted U.S. Pat. No. 6,074,394, the use of pulsed direct current is disclosed in order to attain "metal immunity" (i.e., the ability to determine the position of the object accurately notwithstanding the magnetic field distortion), this embodiment of the present invention is capable of overcoming this difficulty and achieving metal immunity using alternating current.

Figure 11:
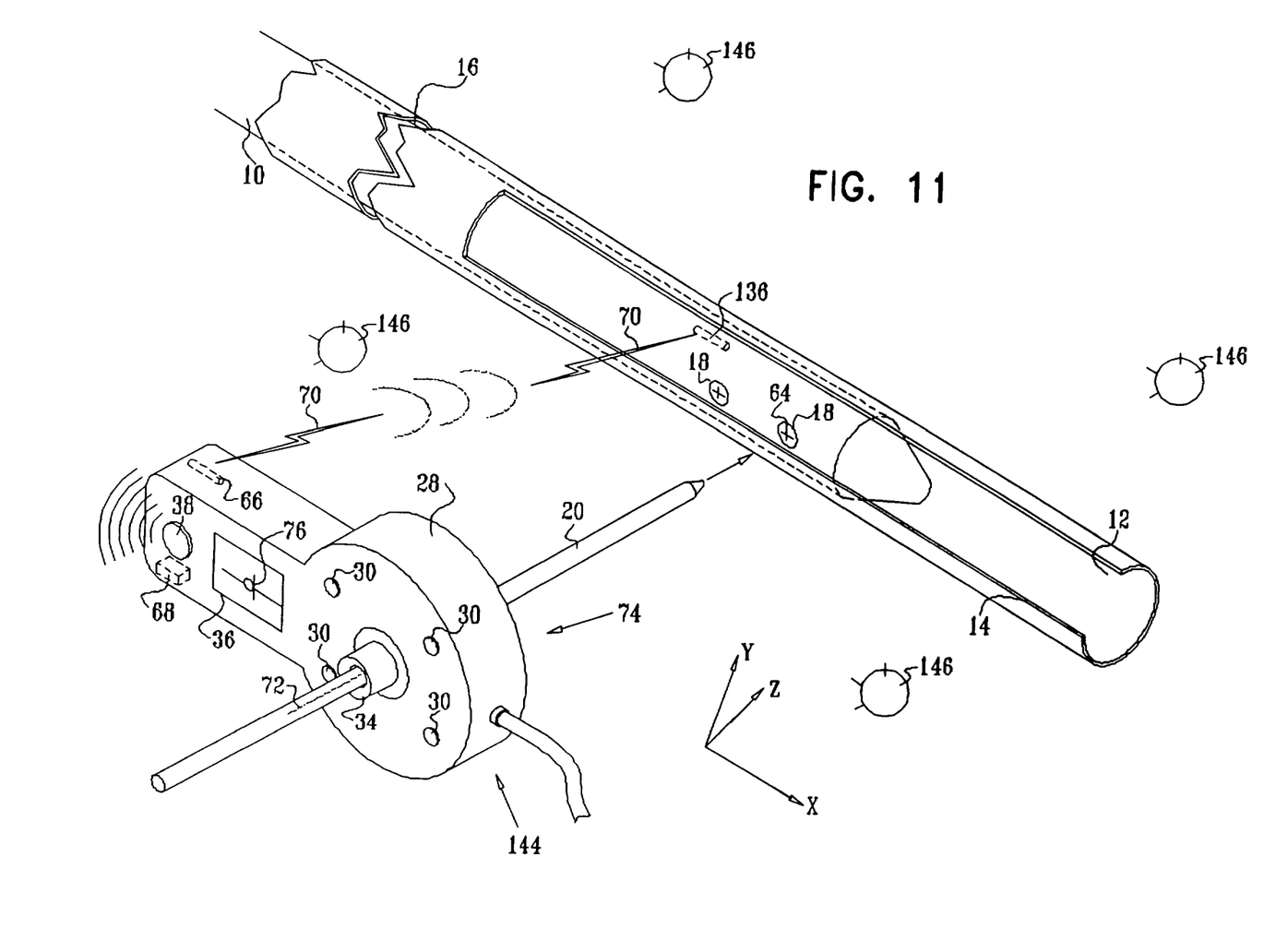
FIG. 11 is a schematic illustration of a distal targeting system which is constructed and operative in accordance with an alternate embodiment of the invention, which includes locating elements to improve metal immunity.

Reference is now made to FIG. 11, which is a schematic illustration of a distal targeting system which is constructed and operative in accordance with an alternate embodiment of the invention. Elements in FIG. 11 that are identical to those of FIG. 1 are given like reference numerals. A magnetic field positioning arrangement 144 is similar to the magnetic field positioning arrangement 22 (FIG. 1), except now, a plurality of locating elements 146 are present. The absolute position of each of the locating elements 146 is preferably known, e.g., by attaching the elements to a reference frame (not shown) which could be attached, for example to an operating table or the like. The locating elements 146 can be wireless sensors similar to the sensor 24, or conventional Hall effect sensors. The positions of the locating elements 146 are determined using the same techniques disclosed hereinabove. Any subsequent changes in the measured positions of the locating elements 146, therefore, reflect an error in the measuring procedure, typically due to field distortion by a magnetic object in the area of operations. The change in the position coordinates of the fixed locating elements 146 can then be used to compensate for the effects of distortion on the coordinates of the sensor 24, using spatial interpolation. While four locating elements 146 are shown in FIG. 11, more locating elements, which are preferably non-coplanar, can be added to improve the accuracy of linear or non-linear interpolation. It is preferable that the locating elements 146 should surround the sensor 24 in 3-dimensions, in order that one of the locating elements 146 is always situated between the magnetic object and the sensor 24.

In a preferred embodiment, changes in the sensed positions of four or more non-coplanar locator elements 22 are calculated, and are used as inputs to a spatial interpolation algorithm. A simple linear example is shown in Table 1, in which the sensor 24 is initially located between two of the locating elements 146, and the guide section 74 is moved from an initial position to a final position.

TABLE 1

|  | Initial Measurement (cm) | Final Measurement (cm) | Corrected |
| --- | --- | --- | --- |
| Element #1 | 0 cm | 0.1 cm | 0 cm |
| Guide | 0.1 cm | 0.5 cm | 0.4 cm |
| Element #2 | 10 cm | 10 cm | 10 cm |

Application of the techniques of this embodiment of the present invention shows that the guide section 74 and the location pad 28 move a different distance relative to the sensor 24, from that which would have been determined without the use of the locating elements 146. Advantageously, the magnetic field positioning arrangement 144 provides compensation even for real-time movements of metal objects within its operational space. Since tools and support equipment are frequently moved during medical procedures, it is preferable to update the measured positions of the locating elements 146 substantially each time that a movement of the guide section 74 relative to the sensor 24 is made, which is accomplished automatically by the signal processing circuitry in the control unit 68.

Since the locating elements 146 have known positions, it is possible to relate the locations of the locating elements 146 to the locations of the guide section 74 and the bore 18. The absolute coordinates of the guide section 74 and the bore 18 and their displacements with respect to each other using a fixed coordinate system can then be displayed.

The second, third and fourth embodiments disclosed hereinabove can also be readily modified to employ the technique disclosed of this embodiment, in order to achieve metal immunity.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art which would occur to persons skilled in the art upon reading the foregoing description.

The invention claimed is:

1. A distal targeting system for determining the location and orientation of an instrument relative to a target, comprising:
   a movable guide assembly for guiding an instrument toward a target;
   a plurality of field generators in said guide assembly that generate known distinguishable fields in response to drive signals;
   one or more sensors disposed at known locations with respect to said target that generate sensor signals in response to said fields, said sensors having known alignments with an axis of said target;
   a signal processor responsive to said drive signals and said sensor signals for producing three location coordinates of a point on said guide assembly and two orientation coordinates of an axis of said guide assembly; and
   a display responsive to said signal processor that provides an indication of a location of said point with respect to said target and of an alignment between said axis of said guide assembly and said axis of said target.

2. The distal targeting system according to claim 1, wherein said display is integral with said guide assembly.

3. The distal targeting system according to claim 1, wherein said display comprises a ball-and-crosshairs indication.

4. The distal targeting system according to claim 1, wherein said sensors are wireless sensors.

5. The distal targeting system according to claim 1, further comprising:
   a control unit; and
   a plurality of external field generators responsive to control signals of said control unit, wherein external fields generated by said external field generators provide power to said sensors.

6. The distal targeting system according to claim 5, wherein said external fields further provide said drive signals to said field generators in said guide assembly.

7. The distal targeting system according to claim 1, wherein said indication comprises five positional and orientation coordinates.

8. The distal targeting system according to claim 1, wherein said target comprises a hollow appliance, and said sensors are insertable therein.

9. The distal targeting system according to claim 8, wherein said target comprises an intramedullary nail.

10. The distal targeting system according to claim 1, wherein said sensors are integral with said target.

11. The distal targeting system according to claim 10, wherein said target comprises an intramedullary nail.

12. The distal targeting system according to claim 1, further comprising a plurality of locating elements having location field detectors therein, said locating elements being disposed at known locations with respect to a fixed frame of reference, wherein said signal processor is responsive to said locating elements to determine a corrected indication of said location of said point.

13. A distal targeting system for determining the location and orientation of an instrument relative to a target, comprising:
   a movable guide assembly for guiding the instrument toward the target;
   a plurality of field generators in said guide assembly that generate known distinguishable fields in response to drive signals;
   one or more sensors disposed at known locations with respect to said target that generate sensor signals in response to said fields, said sensors having known alignments with an axis of said target;
   a signal processor responsive to said drive signals and said sensor signals for producing three location coordinates of a point on said guide assembly and two orientation coordinates of an axis of said guide assembly; and
   a location pad attached to said guide assembly and moveable therewith, responsive to said signal processor that provides a quantitative indication of a distance and a location of said point with respect to said target and of an alignment between said axis of said guide assembly and said axis of said target.

14. The distal targeting system according to claim 13, wherein said sensors are wireless sensors.

15. The distal targeting system according to claim 13, further comprising:
   a control unit; and
   a plurality of external field generators responsive to control signals of said control unit, wherein external fields generated by said external field generators provide power to said sensors.

16. The distal targeting system according to claim 15, wherein said external fields further provide said drive signals to said field generators in said guide assembly.

17. The distal targeting system according to claim 13, wherein said quantitative indication comprises five positional and orientation coordinates.

18. The distal targeting system according to claim 13, wherein said target comprises a hollow appliance, and said sensors are insertable therein.

19. The distal targeting system according to claim 18, wherein said appliance comprises an intramedullary nail.

20. The distal targeting system according to claim 13, wherein said sensors are integral with said target.

21. The distal targeting system according to claim 20, wherein said target comprises an intramedullary nail.

22. The distal targeting system according to claim 13, further comprising a plurality of locating elements having location field detectors therein, said locating elements being disposed at known locations with respect to a fixed frame of reference, wherein said signal processor is responsive to said locating elements to determine a corrected indication of said location of said point.

23. A distal targeting system for determining the location and orientation of an instrument relative to a target, comprising:
   a hand-held movable guide assembly for guiding the instrument toward the target;
   a plurality of field generators in said guide assembly that generate known distinguishable fields in response to drive signals;
   a plurality of sensors disposed at known locations with respect to said target that generate sensor signals in response to said fields, said sensors having known alignments with an axis of said target;
   a signal processor disposed in said guide assembly responsive to said drive signals and said sensor signals for producing three location coordinates of a point on said guide assembly and two orientation coordinates of an axis of said guide assembly; and
   a location pad disposed in said guide assembly, responsive to said signal processor that provides a quantitative indication of a distance and a location of said point with respect to said target and of an alignment between said axis of said guide assembly and said axis of said target, said location pad having a visual display for providing said quantitative indication.

24. The distal targeting system according to claim 23, wherein said display is integral with said guide assembly.

25. The distal targeting system according to claim 23, wherein said display comprises a ball-and-crosshairs indication.

26. The distal targeting system according to claim 23, wherein said sensors are wireless sensors.

27. The distal targeting system according to claim 23, wherein said visual display further provides a qualitative indication of a misalignment between said axis of said guide assembly and said axis of said target.

28. The distal targeting system according to claim 23, further comprising:
   a control unit; and
   a plurality of external field generators responsive to control signals of said control unit, wherein external fields generated by said external field generators provide power to said sensors.

29. The distal targeting system according to claim 28, wherein said external fields further provide said drive signals to said field generators in said guide assembly.

30. The distal targeting system according to claim 23, wherein said quantitative indication comprises five positional and orientation coordinates.

31. The distal targeting system according to claim 23, wherein said target comprises a hollow appliance, and said sensors are insertable therein.

32. The distal targeting system according to claim 31, wherein said appliance comprises an intramedullary nail.

33. The distal targeting system according to claim 23, wherein said sensors are integral with said target.

34. The distal targeting system according to claim 33, wherein said target comprises an intramedullary nail.

35. The distal targeting system according to claim 23, further comprising a plurality of locating elements having location field detectors therein, said locating elements being disposed at known locations with respect to a fixed frame of reference, wherein said signal processor is responsive to said locating elements to determine a corrected indication of said location of said point.

36. A distal targeting system for determining the location and orientation of an instrument relative to a target, comprising:
   a movable guide assembly for guiding the instrument toward the target;
   a plurality of field generators in said guide assembly that generate known distinguishable fields in response to drive signals;
   one or more sensors disposed at known locations with respect to said target that generate sensor signals in response to said fields, said sensors having known alignments with an axis of said target;
   a signal processor disposed in said guide assembly responsive to said drive signals and said sensor signals having a first output responsive to a difference between a location of said target and a location of said guide assembly and second output responsive to a difference between a direction of an axis of said guide assembly and a direction of said axis of said target; and
   a display disposed in said guide assembly responsive to said signal processor that provides a qualitative indication of said first output and said second output.

37. The distal targeting system according to claim 36, wherein said display is integral with said guide assembly.

38. The distal targeting system according to claim 36, wherein said display comprises a ball-and-crosshairs indication.

39. The distal targeting system according to claim 36, wherein said sensors are wireless sensors.

40. The distal targeting system according to claim 36, further comprising:
   a control unit; and
   a plurality of external field generators responsive to control signals of said control unit, wherein external fields generated by said external field generators provide power to said sensors.

41. The distal targeting system according to claim 40, wherein said external fields further provide said drive signals to said field generators in said guide assembly.

42. The distal targeting system according to claim 36, wherein said target comprises a hollow appliance, and said sensors are insertable therein.

43. The distal targeting system according to claim 42, wherein said target comprises an intramedullary nail.

44. The distal targeting system according to claim 36, wherein said sensors are integral with said target.

45. The distal targeting system according to claim 44, wherein said target comprises an intramedullary nail.

46. The distal targeting system according to claim 36, further comprising a plurality of locating elements having location field detectors therein, said locating elements being disposed at known locations with respect to a fixed frame of reference, wherein said signal processor is responsive to said locating elements to determine a corrected indication of said location of said target.

47. A distal targeting system for determining the location and orientation of an instrument relative to a target, comprising:
   a movable guide assembly for guiding the instrument toward the target;

one or more first field elements in said guide assembly;

one or more second field elements disposed at known locations with respect to said target, said first field elements and said second field elements being sensors or field generators, wherein at least one of said first field elements and said second field elements is a said sensor, said field generators generating known distinguishable fields in response to drive signals, and said sensors producing sensor signals in response to said fields, said sensors having known alignments with an axis of said target;

one or more third field elements, said third field elements being said field generators;

a signal processor responsive to said drive signals and said sensor signals for producing three location coordinates of a point on said guide assembly and two orientation coordinates of an axis of said guide assembly; and a display responsive to said signal processor that provides an indication of a location of said point with respect to said target and of an alignment between said axis of said guide assembly and said axis of said target.

48. The distal targeting system according to claim 47, wherein said first field elements are said field generators, and said second field elements are said sensors, said second field elements being responsive to distinguishable fields of said first field elements and said third field elements.

49. The distal targeting system according to claim 47, wherein said first field elements are said sensors, and said second field elements are said field generators, said first field elements being responsive to distinguishable fields of said second field elements and said third field elements.

50. The distal targeting system according to claim 47, wherein said first field elements and said second field elements are said sensors.

51. The distal targeting system according to claim 50, wherein said first field elements and said second field elements are wireless and powered by fields of said third field elements.

52. The distal targeting system according to claim 47, wherein said display is integral with said guide assembly.

53. The distal targeting system according to claim 47, wherein said display comprises a ball-and-crosshairs indication.

54. The distal targeting system according to claim 47, wherein said sensors are wireless sensors.

55. The distal targeting system according to claim 47, wherein said indication comprises five positional and orientation coordinates.

56. The distal targeting system according to claim 47, wherein said target comprises a hollow appliance, and said sensors are insertable therein.

57. The distal targeting system according to claim 56, wherein said target comprises an intramedullary nail.

58. The distal targeting system according to claim 47, wherein said sensors are integral with said target.

59. The distal targeting system according to claim 58, wherein said target comprises an intramedullary nail.

60. The distal targeting system according to claim 47, further comprising a plurality of locating elements having location field detectors therein, said locating elements being disposed at known locations with respect to a fixed frame of reference, wherein said signal processor is responsive to said locating elements to determine a corrected indication of said location of said point.

61. A method for determining the location and orientation of an instrument relative to a target, comprising the steps of:

generating one or more distinguishable fields;

sensing a strength and an orientation of each of said fields at known locations with respect to said target;

providing a movable hand-held guide assembly for directing said instrument to said target;

providing a display on said assembly, said display indicating a location of a point of said assembly relative to said target and of an alignment between an axis of said assembly and an axis of said target; and after performing said step of sensing, calculating three location coordinates of said point relative to said target.

62. The method according to claim 61, wherein said display indicates said location of said point using a ball-and-crosshairs indication.

63. The method according to claim 61, wherein said step of sensing is performed in using wireless sensors.

64. The method according to claim 63, wherein said target comprises a hollow appliance, and said wireless sensors are insertable therein.

65. The method according to claim 63, wherein said target comprises an intramedullary nail.

66. The method according to claim 63, wherein said wireless sensors are integral with said target.

67. The method according to claim 61, wherein said display indicates five positional and orientation coordinates.

68. The method according to claim 61, wherein said step of generating is performed by generating said fields in a proximity of said target, and said step of sensing is performed remote from said target.

69. The method according to claim 61, wherein said step of generating is performed by generating said fields remote from said target, and said step of sensing is performed in a proximity of said target.

* * * * *